(12) United States Patent
Vallet

(10) Patent No.: US 8,590,093 B2
(45) Date of Patent: Nov. 26, 2013

(54) PHYSIOLOGICAL RETRACTOR FOR A TOOTHBRUSH

(75) Inventor: Thierry André Christian Vallet, Saint Priest En Jarez (FR)

(73) Assignee: Thierry Andre Christian Vallet, La Fouillouse (FR)

( * ) Notice: Subject to any disclaimer, the term of this patent is extended or adjusted under 35 U.S.C. 154(b) by 331 days.

(21) Appl. No.: 12/988,498

(22) PCT Filed: Apr. 16, 2009

(86) PCT No.: PCT/FR2009/050715
§ 371 (c)(1),
(2), (4) Date: Jan. 4, 2011

(87) PCT Pub. No.: WO2009/138639
PCT Pub. Date: Nov. 19, 2009

(65) Prior Publication Data
US 2011/0088183 A1    Apr. 21, 2011

(30) Foreign Application Priority Data
Apr. 18, 2008  (FR) ..................................... 08 02181

(51) Int. Cl.
*A61C 17/26* (2006.01)

(52) U.S. Cl.
USPC .............................................................. 15/23

(58) Field of Classification Search
USPC .............................................................. 15/23
See application file for complete search history.

(56) References Cited

U.S. PATENT DOCUMENTS

| 1,593,763 | A | * | 7/1926 | Henderson | 15/23 |
| 1,608,532 | A | * | 11/1926 | Robey | 74/141 |
| 1,693,964 | A | * | 12/1928 | Smith | 15/23 |
| 2,185,229 | A | * | 1/1940 | Scott | 476/15 |

(Continued)

FOREIGN PATENT DOCUMENTS

| DE | 3334841 | 4/1985 |
| EP | 0 046 521 A1 | 3/1982 |
| EP | 0 968 686 A1 | 1/2000 |
| FR | 2 377 173 | 8/1978 |

OTHER PUBLICATIONS

International Search Report in connection with International patent application No. PCT/FR2009/050715.

*Primary Examiner* — Mark Spisich
(74) *Attorney, Agent, or Firm* — John P. White; Cooper & Dunham LLP

(57) ABSTRACT

This invention provides a toothbrush comprising:
  a.) a support member of the handle type;
  b.) at least one brushing member mounted to rotate on said support member about an axis of rotation (X-X'), and having side surface that extends along the axis of rotation between a proximal end facing towards the support member, and an opposite, distal end, and that is designed to be brought into contact with the teeth for the purpose of cleaning them; and
  c.) a physiological retractor covering said side surface in part so as to protect the mucous membranes adjacent to the teeth from the mechanical action of the brushing member;

Said toothbrush being characterized in that, facing the side surface of the brushing member, the physiological retractor has a retraction portion.

15 Claims, 2 Drawing Sheets

(56) References Cited

U.S. PATENT DOCUMENTS

| | | | |
|---|---|---|---|
| 2,662,239 A * | 12/1953 | Grover | 15/23 |
| 2,840,837 A * | 7/1958 | Gustems | 15/23 |
| 3,029,451 A * | 4/1962 | Barr | 15/23 |
| 3,033,197 A | 5/1962 | Barckley | |
| 3,739,416 A | 6/1973 | Kurachi | |
| 4,344,202 A * | 8/1982 | Hayat | 15/4 |
| 5,044,035 A * | 9/1991 | Barradas | 15/23 |
| 2006/0230555 A1 | 10/2006 | Yang et al. | |

* cited by examiner

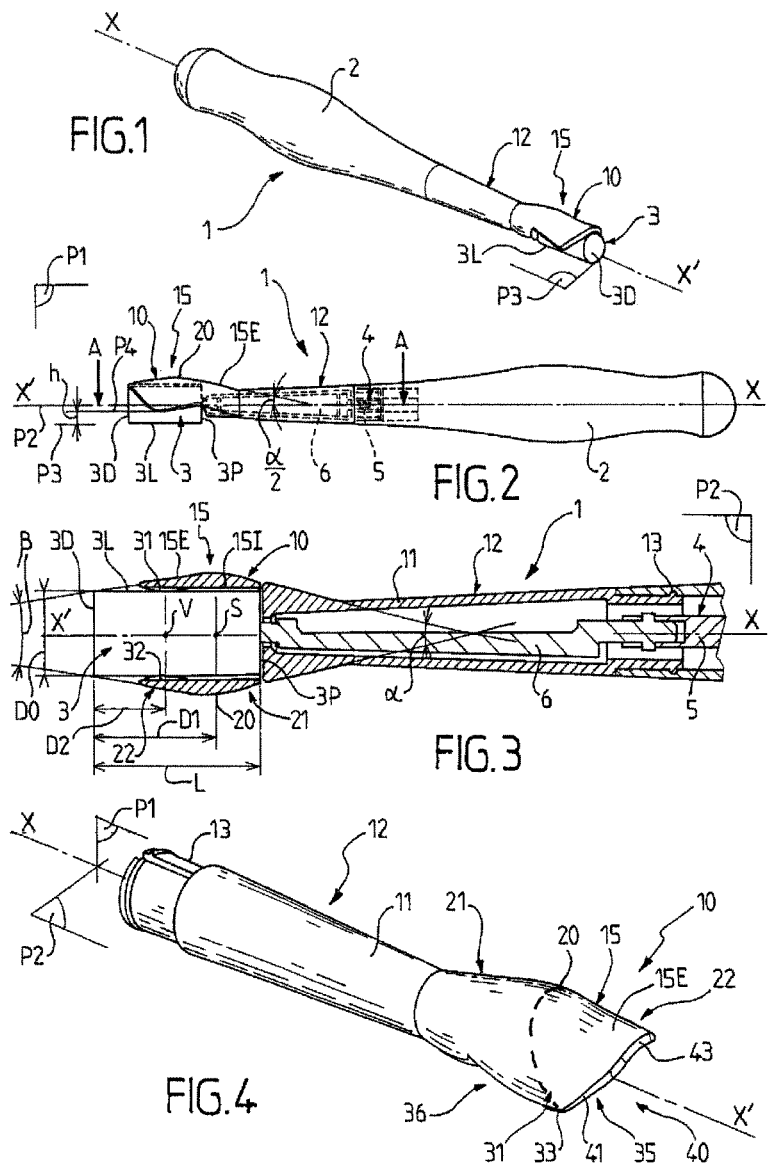

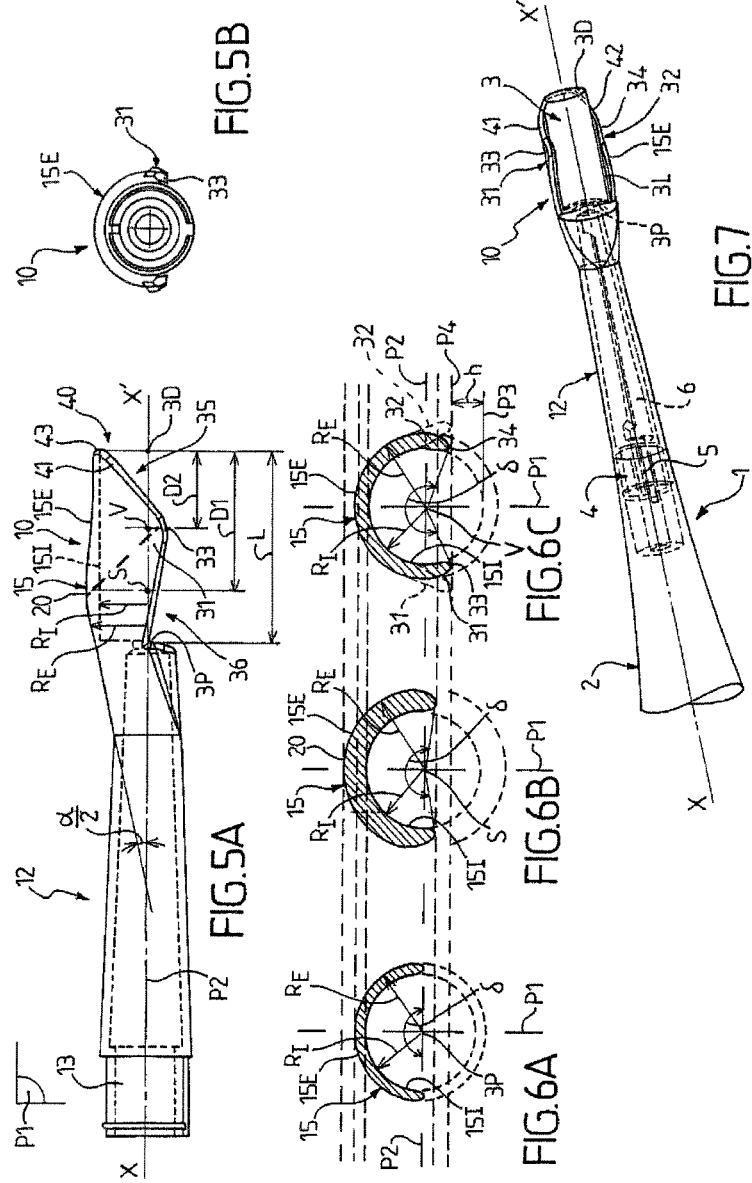

PHYSIOLOGICAL RETRACTOR FOR A TOOTHBRUSH

This application is a §371 national stage of PCT International Application No. PCT/FR2009/050715, filed Apr. 16, 2009, claiming priority of French Patent Application No. 0802181, filed Apr. 18, 2008, the contents of all of which are hereby incorporated by reference into this application.

TECHNICAL FIELD

The present invention relates to the general field of dental hygiene, and more particularly to the field of toothbrushes for human or veterinary use.

The present invention relates in particular to a toothbrush comprising:
- a support member of the handle type;
- at least one brushing member for brushing teeth, which member is mounted to rotate on said support member about an axis of rotation (X-X'), said brushing member having a side surface that extends along its axis of rotation (X-X') between a proximal end facing towards the support member, and an opposite, distal end, said side surface being designed to be brought into contact with the teeth for the purpose of cleaning them by mechanical action; and
- a physiological retractor covering said side surface in part so as to protect the mucous membranes adjacent to the teeth from the mechanical action of the brushing member.

PRIOR ART

Brushing the teeth constitutes a long-standing dental hygiene practice aimed at removing both food deposits and dental plaque that might give rise to dental calculus or "tartar", or indeed to foci of infection.

To that end, it is known, in particular, that electric toothbrushes can be used. Such a toothbrush is provided with a motor that rotates a brushing member that is generally constituted by a brush having synthetic bristles.

In certain prior art toothbrushes, the brushing member is mounted to extend the handle in such a manner as to be substantially in alignment therewith.

Thus, the brushing action can be performed by approaching the teeth tangentially, using the "roll" or "rolling stroke" method, i.e. brushing in the direction going from the gum to the tooth.

Although such a brushing mode is particularly effective and gentle on the gums, toothbrushes of that type suffer from the drawback of simultaneously exerting an abrasive action on the adjacent mucous membranes, in particular on the cheeks or the lips, and that abrasive action can damage those mucous membranes.

In order to remedy that drawback, proposals have been made to cover the brushing member in part with a stationary plate or shell forming a physiological retractor that acts as a screen between the moving brush and the mucous membrane.

Although prior art physiological retractors improve brushing comfort by protecting the mucous membranes to a relatively satisfactory extent, they suffer from certain non-negligible drawbacks.

Known physiological retractors are generally in the form of a semi-cylindrical shell that is relatively voluminous and that masks to a large extent the working surface of the brushing member.

Therefore, known retractors tend to hinder access by the brushing member to the teeth, in particular in the narrow or remote zones of the mouth, and naturally that can be detrimental to the overall effectiveness of the brushing.

Furthermore, the additional volume occupied by the head of the toothbrush due to the presence of said retractor is a source of discomfort during brushing.

SUMMARY OF THE INVENTION

Objects assigned to the invention are therefore to remedy the above-mentioned drawbacks and to propose a novel toothbrush that enables brushing to be effective, comfortable and gentle not only on the teeth and on the gums but also on the adjacent mucous membranes.

Another object assigned to the invention is to propose a novel toothbrush that has a particularly simple and compact structure, and that is inexpensive to manufacture.

Objects assigned to the present invention are also to propose a novel toothbrush that is particularly simple, intuitive, and safe to use.

Finally, another object assigned to the invention is to propose a novel toothbrush that can easily access all of the zones of the mouth that need to be brushed, without generating any discomfort or pain or injury for the user.

The objects assigned to the invention are achieved by means of a toothbrush comprising:
- a support member of the handle type;
- at least one brushing member for brushing teeth, which member is mounted to rotate on said support member about an axis of rotation (X-X'), said brushing member having a side surface that extends along its axis of rotation (X-X') between a proximal end facing towards the support member, and an opposite, distal end, said side surface being designed to be brought into contact with the teeth for the purpose of cleaning them by mechanical action; and
- a physiological retractor covering said side surface in part so as to protect the mucous membranes adjacent to the teeth from the mechanical action of the brushing member;

said toothbrush being characterized in that, facing the side surface of the brushing member, the physiological retractor has a retraction portion, and the distance from the outside surface of said retraction portion to said axis (X-X') varies along the axis of rotation (X-X') in such a manner as to form a bulge, and in that said physiological retractor has a beveled distal portion forming a penetration tip.

BRIEF DESCRIPTION OF THE DRAWINGS

Other objects, characteristics and advantages of the invention appear in more detail on reading the following description and on examining the accompanying drawings that are given merely by way of non-limiting illustration, and in which:

FIG. 1 is an overall perspective view of a variant embodiment of a toothbrush of the invention;

FIG. 2 is a side view of the FIG. 1 toothbrush;

FIG. 3 is a side view partially in section on A-A, showing a portion of the toothbrush shown in FIGS. 1 and 2;

FIG. 4 is a perspective view of a variant embodiment of a physiological retractor of the invention that can be used on the toothbrush shown in FIGS. 1 to 3;

FIGS. 5A and 5B are respectively a side view and a rear view of the physiological retractor shown in FIG. 4;

FIGS. 6A, 6B, and 6C are three sections of the physiological retractor shown in FIGS. 4 and 5A, at different positions along the axis (X-X'); and FIG. 7 is a perspective view from below, showing a portion of the toothbrush shown in FIGS. 1 to 3.

BEST MANNER OF IMPLEMENTING THE INVENTION

The present invention relates to a toothbrush 1 designed to maintain dental hygiene by mechanically eliminating food deposits and dental plaque.

The present invention relates in particular to a toothbrush 1 for human use, but it may equally be adapted to veterinary use, in particular for farm animals or for pets (dogs, horses, cattle, sheep, pigs, goats, etc.).

In conventional manner, the toothbrush 1 has a support member 2 that is provided with at least one brushing member 3 for brushing teeth.

In the meaning of the invention, the support member 2 enables the user of the brush to manipulate the brush member 3, and in particular substantially to control its position and its orientation in three dimensions, and to control the pressure with which it comes into contact with the teeth and/or with the gums.

Naturally, said support member 2 is in no way limited to any one particular embodiment, and could, in particular, be provided with a grip or with a hinged arm.

However, particularly preferably, the support member 2 is designed to make it possible to take hold of the toothbrush 1 directly, and thus constitutes a handle.

Preferably, said support member 2 is substantially elongate and, in particular, it can be substantially in the form of a stick that is circularly symmetrical in shape and that optionally has one or more bulges designed to form an ergonomic grip making it easier to take hold of, as shown in FIGS. 1 and 2.

In accordance with the invention, the brushing member 3 is mounted to move in rotation on the support member 2, about an axis of rotation (X-X').

More particularly, said brushing member 3 has a side surface 3L that extends along its axis of rotation (X-X') between a proximal end 3P that faces towards the support member 2, and an opposite, distal end 3D.

Said side surface 3L is designed to be brought into contact with the teeth so as to clean them by mechanical action.

To this end, the brushing member 3 preferably has a slightly abrasive flexible covering having an outside surface that corresponds to the side surface 3L and that is designed to come into contact with the teeth and with the gums.

The abrasive covering may, in particular be formed by a plurality of bristles, preferably made of a synthetic material, and projecting substantially radially relative to a core made of a rigid material and having its axis coinciding with the axis of rotation (X-X').

Naturally, the diameter, the length, the shape, and the flexibility or "softness" of the bristles are defined by the person skilled in the art as a function of the use for which the brush is designed, and in particular as a function of the sensitivity of the user.

Naturally, the bristles or tufts of bristles constituting the abrasive covering may be of equal length or of different lengths, and may be mutually touching or spaced apart from one another, the physical surface of the brushing member 3 then having unevenness in its outline, e.g. an alternation of indentations and of projections, or indeed having interstices of the "hole" type.

For convenience of description, it is considered that, in the meaning of the invention, the side surface 3L refers to the geometrical envelope, lying between the proximal end 3P and the distal end 3D, and within which the abrasive covering constituting the brushing member 3 lies.

Preferably, said geometrical envelope, and more particularly the brushing member 3, is substantially circularly symmetrical in shape about the axis of rotation (X-X'), or at least of shape that does not vary by rotation (e.g. of order 1, 2, etc.) about said axis.

In particular, the brushing member 3 can be of substantially cylindrical shape, preferably right cylindrical, of circular base, and of axis (X-X').

When the geometrical envelope and more particularly the brushing member 3 is formed by such a cylinder of axis (X-X'), the side surface 3L defines the curved side wall of said cylinder, while the proximal end 3P and the distal end 3D correspond to the plane circular base surfaces of said cylinder that are normal to the axis (X-X').

Naturally, variations on the shape of the brushing member 3 are possible, it being possible for the brushing member 3 to have a cross-section that is constant or that varies along the axis (X-X'), and in particular to have an undulating profile, or to be egg-shaped or ellipsoidal with a proximal end 3P and a distal end 3D that form poles.

In addition, the length L of the brushing member 3 is preferably significantly greater than its overall diameter D0.

Thus, by way of example, the length L may lie in the range 15 millimeters (mm) to 30 mm, and preferably be about 25 mm, while the overall diameter D0 (i.e. the diameter measured in the widest section) may lie in the range 12 mm to 15 mm, and preferably be substantially equal to 12 mm.

Particularly preferably, the axis of rotation (X-X') is situated substantially in longitudinal alignment with the support member 2, i.e. substantially parallel to, and preferably coinciding with the main direction in which said support member 2 extends.

Thus, as shown in FIGS. 1 to 3 and 7, the brushing member 3 substantially forms a "longitudinally rotary" brush.

Such a toothbrush advantageously makes it possible to perform tangential brushing using the "roll" or "rolling stroke" method, i.e. in a sweeping movement from the gum towards the tooth, that advantageously combines mechanically effective brushing with gentleness on the gums.

In other words, the toothbrush 1 is arranged such that, during the brushing, the user can bring the side surface 3L of the brushing member 3 in a tangential approach against the surface of the tooth, the axis of rotation (X-X') being substantially parallel to the main direction in which the gum extends.

Advantageously, the toothbrush 1 of the invention is also provided with drive means 4 capable of driving the brushing member 3 in rotation about its axis (X-X') by transmitting to said brushing member sufficient speed and torque to enable it to exert its mechanical action for cleaning by friction on coming into contact with the teeth.

In a preferred embodiment, shown in particular in FIGS. 3 and 7, the drive means 4 may comprise an electric motor, the outlet shaft 5 of which is in engagement with a transmission element 6 of the spindle type connected to the brushing member 3.

Preferably, the drive means 4 are arranged to drive the brushing member 3 continuously, i.e. to enable said brushing member to rotate through any number of consecutive turns in the same direction.

In addition, said drive means 4 are advantageously bi-directional, i.e. they are provided with reversal means enabling the user to chose, alternatively, one direction of rotation or the other direction of rotation for the brushing member 3 about the axis (X-X'), depending on whether the user is brushing the labial or the lingual faces of the teeth, and depending on whether the teeth are situated on the lower jaw or on the upper jaw.

Furthermore, the drive means 4 are preferably provided with a speed regulator (not shown) designed to enable the user to choose the speed of rotation of the brushing member 3, e.g. within the range 30 revolutions per minute (rpm) to 180 rpm.

In accordance with an important characteristic of the invention, the toothbrush 1 is also provided with a physiological retractor 10 that covers in part the side surface 3L of the brushing member 3, so as to protect the mucous membranes adjacent to the teeth from the mechanical action of said brushing member 3, while said brushing member is being moved in rotation.

Naturally, said physiological retractor 10 is advantageously drivingly independent from the brushing member 3 so as not, itself, to be driven in rotation by the drive means 4.

Preferably, the physiological retractor 10 is fastened to the support member 2, and is preferably formed integrally therewith, and more particularly with a neck portion 11 that forms the head 12 of the toothbrush 1.

Naturally, the physiological retractor 10 is preferably made of a material that is sufficiently rigid to enable it to exert a retraction and retaining force against the mucous membranes, and said retractor is preferably made of a polymer material.

Preferably, as is shown, in particular, in FIGS. 3 and 4, the head 12 of the toothbrush 1 is removable, and, for this purpose, is provided with reversible fastening means 13 enabling it to be fastened, e.g. by interfitting or clipping, to the support number 2.

Advantageously, it is thus possible to replace the head 12 as a function of the needs of the user or indeed as a function of the state of wear of the brushing member 3.

In accordance with an important characteristic of the invention, facing the side surface 3L of the brushing member 3, the physiological retractor 10 has a retraction portion 15, and the distance $R_E$ from the outside surface 15E of said retraction portion to the axis of rotation (X-X') varies along said axis (X-X').

In other words, the overall cross-sectional dimension of the physiological retractor 10, as measured in a plane normal to the axis (X-X') does not have a constant value as a function of the abscissa value of said plane, when the abscissa value of said plane is caused to vary along the axis (X-X') between the abscissa value of the distal end 3D and the abscissa value of the proximal end 3P of the brushing member 3.

More particularly, the outside outline of the physiological retractor 10 of the invention, as projected in the "sagittal" plane P1 of the toothbrush 1, is not parallel to the axis (X-X') in its portion situated in register with the side surface 3L of said brushing member 3, i.e. the points making up said outline do not lie at a constant radius $R_E$ from said axis (X-X') when travelling along said outline in a direction corresponding to the direction of said axis (X-X').

Advantageously, this geometrical feature of the physiological retractor 10 of the invention simplifies inserting the toothbrush into the mouth, between the teeth and the mucous membranes, and improves keeping the mucous membranes away from the active brushing zone without causing any major discomfort to the user.

In a variant embodiment (not shown), the physiological retractor 10 may be formed by a curved plate of substantially constant thickness.

However, particularly preferably, and as shown in particular in FIG. 2, 3 or 5A, the inside wall 15I of the retraction portion 15, and more generally of the physiological retractor 10 as a whole, defines, while delimiting it at least in part, a recess 16 of substantially cylindrical shape and of substantially constant diameter, designed to receive a cylindrical brushing member 3, or at least a brushing member that lies within a cylinder.

To this end, the distance $R_I$ from the axis to the inside wall 15I is chosen so as to enable said brushing member 3 to move in rotation, preferably with a small amount of residual clearance, in the resulting recess.

In such a variant embodiment, and as shown in FIGS. 5A, 6A, 6B, and 6C, while the measurement of the distance $R_I$ between the axis (X-X') and the inside surface 15I, i.e. the radius $R_I$, remains substantially constant, the variation in the measurement of the distance $R_E$ between said axis (X-X') and the outside surface 15E results in a variation in the thickness of the physiological retractor 10, in its portion lying facing the side surface 3L.

In addition, although the retractor 10 may be perforated in its thickness, it is preferably solid.

Naturally, the outline of the outside surface 15E is in no way limited to any particular variant embodiment, and it may, in particular, have a substantially flared shape, e.g. a continuously frustoconical shape, or indeed an alternation of projecting and recessed elements (projections and indentations) or indeed of undulations.

However, particularly preferably, the outside surface 15E of the retraction portion 15 is provided with at least one bulge 20.

In other words, the physiological retractor 10 has at least one protuberance that projects outwardly from the "dorsal" face of the toothbrush that faces "upwards" in FIG. 2, i.e. that is substantially opposite, about the axis of rotation (X-X'), from the "ventral" face that faces "downwards" in FIG. 2, and at which the brushing member 3 is visible and can approach the teeth tangentially.

Preferably, the bulge 20 also extends over either one of or both of the "sides" of the physiological retractor, as shown in FIG. 3 or in FIG. 5B.

In particularly advantageous manner, the convex profile of the outline of the physiological retractor 10 imparts an outwardly arched shape to it, at least in a zone that is preferably diametrically opposite from the active zone of the brushing member 3, thereby enabling it to have a sort of bead of material forming a substantially annular retraction surface of the hoop type, whose "crest line" is shown in dashed lines in FIG. 4, or more "scrunched up" and of the tent pole type, that comes to support the mucous membrane and to hold it away from said active zone during the brushing.

In accordance with a characteristic that is shown in FIGS. 4 and 5B, and, that can also constitute an invention in itself, the bulge 20 may form a hoop that is inclined relative to the axis of rotation (X-X'), and more generally relative to the longitudinal direction of extension of the physiological retractor 10 and of the toothbrush.

In other words, the crest line corresponding to the culminating outline of the bulge 20 and that extends substantially in a U-shape about the axis (X-X') from one side edge of the retractor 10 to the other by going via the dorsal portion of said retractor, is preferably disposed on a slant relative to said axis, and preferably lies substantially in a plane that is not normal to said axis. The angle formed between the projection of the crest line and the sagittal plane P1 of the toothbrush 1, and more particularly between the plane containing said crest line and the sagittal plane of the retractor 10 may, in particular lie in the range 45° to 60°.

Preferably, said hoop "leans backwards", i.e. the dorsal portion of the crest line (the base of the U-shape) is set back towards the handle relative to its two side ends (the branches of the U-shape) that point in the opposite direction, towards the distal portion of the brushing member 3.

Particularly preferably, the physiological retractor 10 is provided with a single bulge 20 in the zone lying between the proximal end 3P and the distal end 3D, said bulge therefore forming the culmination of the retraction portion 15.

In other words, the distance $R_E$ to the axis (X-X') from the outside surface 15E preferably increases from the proximal end 3P up to the maximum of the bulge 20, and then decreases down to the free distal end of the physiological retractor 10.

Preferably, with the brushing member 3 having a length L as measured from its proximal end 3P to its distal end 3D, the bulge 20 culminates, at least on the dorsal face of the retractor 10, in register with a point S on the axis of rotation (X-X') that is situated at a distance D1 lying in the range 0.5×L to 0.9×L from the distal end 3D, and preferably in the range 0.65×L to 0.80×L from the distal end 3D.

The phrase "in register with" is used to indicate that the point in question is projected orthogonally from the outside surface 15E onto the axis (X-X').

In other words, the bulge 20 is closer to the handle than to the free end of the toothbrush, the ratio D1/L preferably lying in the range 50% to 90%, and particularly preferably in the range 65% to 80%.

Preferably, as shown in FIGS. 2 to 6C, the retraction portion 15 has at least a first segment 21 that has a substantially frustoconical outside surface.

More particularly, said first segment 21 can connect a constricted portion of the neck 11 to a base, the edge of which marks the bulge 20, preferably by flaring continuously, i.e. without presenting a concave zone forming a setback. The first segment 21 can thus form a proximal segment.

Naturally, the generator lines of the frustoconical envelope within which the outside surface of the first segment 21 lies, and preferably with which said outside surface coincides, may be rectilinear or curved, in particular slightly outwardly bowed.

By way of example, the aperture angle α of the first segment 21, i.e. the angle at the vertex of the truncated cone that generates it preferably lies substantially in the range 20° to 30°.

Thus, the distance to the axis $R_E$ from the outside surface 15E, and more particularly the radius $R_E$ generating said surface in a plane normal to the axis (X-X') preferably increases continuously from the proximal end 3P to the bulge 20.

Over said first segment 21, the cavity defined by the inside surface 15I of the physiological retractor 10 preferably has a right cylindrical geometrical shape, i.e. a radius $R_I$ that is substantially constant.

In a preferred variant embodiment, the retraction portion 15 also has at least a second segment 22 that has an outside surface that is substantially frustoconical. Preferably, said second segment 22 forms a distal segment, placed in alignment with the first segment along the axis (X-X').

Preferably, the angle at the vertex β of the second frustoconical segment 22 also lies substantially in the range 10° to 20°.

As shown in the figures, the first and second segments 21, 22 preferably extend in opposite directions and are preferably joined together via their common base so that the outside surface 15E of the retraction portion 15 has a substantially bi-conical shape.

In other words, the outside surface 15E of the retraction portion 15 is preferably formed by a shell that is substantially bi-conical, of circular base, and of axis coinciding with the axis of rotation (X-X') of the brushing member 3, said shell being recessed in its "ventral" portion, i.e. in such a manner as to open out with clearance for the brushing member 3 at the working surface of said brushing member 3 that comes into contact with the teeth.

To this end, it is remarkable that the join between the first and second segments 21, 22 at their base may advantageously lie substantially in a plane that is normal to the axis (X-X') when the hoop corresponding to the bulge 20 is perpendicular to said axis, or indeed it may extend in a direction slanting relative to said axis (X-X) and more particularly lie in a plane that is inclined relative thereto, as shown in FIG. 4.

In addition, in accordance with a preferred characteristic that can constitute an invention in its own right, and independently of the presence of a retraction portion 15 of the invention, the angular coverage δ of the physiological retractor 10 about the axis of rotation (X-X'), facing the side surface 3L of the brushing member 3, varies along said axis (X-X').

In other words, the circular arc defined or at least covered by the physical retractor 10 in a plane normal to the axis of rotation (X-X') varies as a function of the abscissa value of said plane, i.e. of the position along said axis (X-X') of the point at which the plane intersects with said axis, as shown in FIGS. 6A, 6B, and 6C.

Preferably, this variation in the angular coverage is observed in the retraction portion 15, i.e. between the proximal end 3P and the distal end 3D of the brushing member 3.

Thus, the physiological retractor 10 may advantageously substantially have the shape of a curved plate that shrouds the side surface 3L of the brushing member 3 in a manner that is different, i.e. that is not constant, as a function of the point in question along said brushing member 3.

More particularly, the physiological retractor 10 may have a first cheek 31 and a second cheek 32 that are disposed on either side of the brushing member 3 about the axis of rotation (X-X') in such a manner that the angular coverage δ of the corresponding cross-section is greater than 180°, and is preferably strictly greater than 180° and less than or equal to 190°, as shown, in particular in FIG. 6C.

In other words, the cheeks 31, 32 extend the dorsal portion of the physiological retractor 10 that lies above the midplane P2 containing the axis of rotation (X-X') and perpendicular to the sagittal plane P1, and said cheeks extend beyond said midplane P2, "below" said midplane, opposite from said dorsal portion and towards the ventral portion of the toothbrush 1.

Thus, the cheeks are advantageously "wrap-around", and they flank, at least on part, the middle zones of the side surface 3L.

Naturally, the cheeks 31, 32 of the invention are not limited to any one particular embodiment.

In particular, they may have curved surfaces, as shown in the figures, and in particular, inside faces substantially extending on from the inside surface 15I of the dorsal portion with substantially the same inside radius $R_I$. In a variant embodiment (not shown), each of the cheeks may have a substantially plane surface, forming a right tangential extension by extending "downwards" substantially vertically from the midplane P2, along a straight line that is tangential to the circle of radius R.

In another variant corresponding to FIGS. 4 and 5B, and shown in dashed lines in FIG. 6C, the cheeks may correspond to the side ends of the inclined crest line of the bulge 20, said cheeks tending to extend away from the axis (X-X') so as to form a flare in the cross-section of the retractor 10 towards the ventral face of the brushing member 3.

Particularly preferably, the first and second cheeks 31, 32 are provided, along the axis (X-X'), respectively with a first antinode 33 and with a second antinode 34 that constitute the low points of the physiological retractor 10.

Preferably, each cheek has a single antinode in the space lying between the proximal end 3P and the distal end 3D.

Advantageously, said first and second antinodes 33, 34 "culminate", i.e. reach their free ends, between the midplane P2 and a working plane P3 that extends parallel to said midplane P2 and that is tangential to the working (active) ventral face of the brushing member 3, i.e. to the envelope of the side wall 3L.

Thus, said antinodes are placed set back from said working plane P3 that, in practice, substantially corresponds to the contact plane in which the brushing member 3 comes into contact with the surface of the tooth.

In other words, the low points of the physiological retractor 10 constitute the zones of the physiological retractor that are the closest to the surfaces of the teeth during the brushing, but they are arranged set back relative to the brushing member 3, "above" said brushing member, in order to leave said brushing member 3 to protrude ventrally relative to the physiological retractor.

In particularly advantageous manner, the antinodes 33, 34 thus form penetration-limiting means arranged to come into abutment against the surfaces of the teeth (or against the surface of the gum), when the brushing member 3 approaches said teeth in an approach movement that is substantially radial to the axis (X-X').

Thus, when the brushing member 3 is brought into contact with the teeth and when the user exerts substantially radial penetration pressure, via the handle, in order to hold the brushing member 3 pressed against said teeth, said brushing member 3, and more particular its flexible covering, can deform by being crushed against the surfaces of the teeth or of the gum and/or work its way into the interstices between the teeth until the first and the second antinodes 33, 34 come into abutting contact against the surface of the teeth, or against the surface of the gum, thereby stopping the penetration movement.

The antinodes 33, 34 thus make it possible to limit the maximum depth h of penetration or of crushing of the brushing member 3, and therefore to limit the maximum pressure exerted radially by the brushing member 3 on the gum or on the surfaces of the teeth.

By way of example, the maximum depth of penetration h may be set in the range 2 mm to 6 mm.

Advantageously, such an arrangement of abutments makes it possible to guarantee that brushing is both effective, because the brushing member 3 is brought into pressing contact against the teeth, and also gentle on the tissues due to the fact that the antinodes guarantee that the brushing action is not exerted with too much pressure being applied.

Naturally, the antinodes 33, 34 are of non-traumatic shape, and in particular with rounded edges, so as not to injure the teeth or the gums when said antinodes come into contact thereagainst.

Thus, in accordance with a characteristic that can constitute an invention in its own right, the toothbrush 1 is thus preferably provided with penetration-limiting means suitable for enabling the working penetration or the working resilient crushing of the brushing member 3 to take place against the teeth in a direction transverse to its axis of rotation (X-X'), while also limiting the maximum amplitude of said penetration or crushing to a level that is not traumatic for the teeth and for the gums.

Particularly preferably, and as shown in the figures, the physiological retractor 10, and more generally the toothbrush 1 is symmetrical about the sagittal plane P1.

Thus, the first and second cheeks 31, 32, and more particularly the first and second antinodes 33, 34, are superposable in projection in the sagittal plane P1.

Preferably, the low points formed by the first and second antinodes 33, 34 are situated in register with a point V on the axis of rotation (X-X') that is situated at a distance D2 lying in the range $0.3 \times L$ to $0.5 \times L$ from the distal end 3D, and preferably substantially equal to $0.4 \times L$ from the distal end 3D.

Thus, as shown, in particular in FIG. 5A, the antinodes 33, 34 are preferably offset towards the distal end 3D relative to the maximum of the bulge 20.

Advantageously, the crest line corresponding to the hoop formed by the bulge 20 can thus join the antinodes 33, 34 together by going via the dorsal maximum of the bulge 20, opposite from the active ventral face of the brushing member 3, and thus find itself inclined "backwards".

In a preferred variant embodiment that can constitute an invention in its own right, the physiological retractor 10 has a first clearance zone 35 and a second clearance zone 36 that are disposed on either side of each antinode 33, 34 along the axis of rotation (X-X'), so as to allow the physiological retractor 10 and the brushing member 3 a certain amount of clearance so that they can rock to some extent about an axis that is transverse to said axis of rotation (X-X'), without causing said physiological retractor 10 to interfere with the gum or with the teeth.

Geometrically, the physiological retractor 10 can thus come into abutment, at the antinodes 33, 34 against a stationary geometrical gauge plane P4 that is parallel to the midplane P2 and tangential to the maxima of the antinodes 33, 34 (and thus that is situated at a distance h from the working plane P3) when the toothbrush 1 is at rest with its axis (X-X') horizontal, and rock forwards and backwards on said antinodes through a predetermined pitch amplitude, measured between the axis (X-X') and the gauge plane, e.g. in the range 10° to 20°, without the physiological retractor 10 going beyond said set gauge plane.

Preferably, in projection in the sagittal plane P1, each antinode 33, 34 has a substantially V-shaped outline with a rounded base, so that, even when the physiological retractor 10 comes into abutment against the tooth or the gum at said antinodes, it continues to have the possibility of rocking slightly forwards or backwards, i.e. of accommodating the rocking movements imparted by the handle 2 when said handle acts as a lever.

Thus, the brushing member 3 can advantageously be brought into contact with the entire surfaces of the teeth, in spite of the natural relief, such as protuberances or depressions, of said surfaces.

In a variant embodiment that can constitute an invention per se, the physiological retractor 10 has a beveled distal portion 40 that forms a penetration tip.

Advantageously, such a slanting penetration tip facilitates engaging the physiological retractor 10 into the mouth, and in particular between the gums and the mucous membranes.

As shown in FIGS. 4 and 5A, the beveled distal portion 40 is preferably arranged such as to uncover most of and preferably all of the face forming the distal end 3D of the brushing member 3.

In other words, the profile of the bevel of the distal portion 40, projected in the sagittal plane P1, preferably extends on either side of the midplane P2.

Thus, preferably, the physiological retractor 10 is open at its distal end so as to expose most of and preferably all of the distal end 3D of the brushing member 3, said brushing member being cantilevered out relative to the support member 2.

Advantageously, the beveled distal portion 40 may coincide with the above-described first clearance zone 35.

More particularly, the penetration tip is preferably made up of two engagement ramps 41, 42, each of which connects the antinode 33, 34 of a respective one of the cheeks 31, 32 to the free distal end 43 of the physiological retractor 10.

Said engagement ramps 41, 42 can thus form a gentle transition between said free distal end 43 situated on the dorsal face of the physiological retractor and a corresponding antinode 33, 34 situated on the other side of the midplane P2, towards the ventral face of said physiological retractor.

Thus, the retractor 10 advantageously opens out on its ventral face, while giving clearance for the active zone of the brushing member 3 by means of a beveled portion 40 extending "downwards" from the dorsal distal portion of said retractor towards the ventral proximal portion thereof.

Naturally, the penetration tip, and more particularly the engagement ramps 41, 42 and the free distal edge 43 are preferably edged by a rounded fender so as to be non-traumatic.

Particularly preferably, the physiological retractor 10 does not extend beyond the distal end 3D of the brushing member 3 along the axis (X-X');

In other words, the free distal edge 43 of said physiological retractor 10 that is situated at the tip thereof terminates substantially in register with the brushing member 3, in a manner flush with or slightly set back from the distal end 3D.

Advantageously, the overall size of the physiological retractor 10 is thus confined to the minimum necessary and sufficient for protecting the mucous membranes at the dorsal face, without increasing the overall size of the toothbrush along its longitudinal axis (X-X').

In particular, no element of the end shield or bearing type projects longitudinally beyond the distal end of the brushing member 3.

In a preferred variant embodiment shown, in particular in FIGS. 2 and 3, the toothbrush 1 of the invention has a modular structure, and can, in particular be constituted firstly by a handle 2 containing the rotary drive means 4 and secondly by a removable head 12 such as described above.

Therefore, the invention also relates to a replacement head for a toothbrush, which head is provided with a brushing member 3 and with a physiological retractor 10 of the invention.

Naturally, the invention may also relate, per se, to a physiological retractor 10 as described above, designed to be mounted on a toothbrush by means of suitable fastening means, it being possible for such a physiological retractor 10 to be used as a retrofit on a prior art toothbrush.

Thus, advantageously, the toothbrush 1 of the invention enables the brushing member 3 to be inserted gently into the mouth and to be brought gently to the zone to be cleaned, the insertion tip and the slope formed by the outside surface of the second frustoconical segment 22 making it possible, by a wedging effect, for the flexible mucous membrane (lip, tongue, or cheek) to be retracted gradually from the teeth and from the gum, and then for said mucous membrane to be held away from the teeth, at the bulge 20 in the retraction portion 15, i.e. opposite from the active zone of the brushing zone.

In particular, the fact that it is preferably in the shape of a bell or of a horn that opens onto the distal and ventral portions of the brushing member makes it possible for the mucous membranes to be retracted and held away effectively, while also preserving excellent accessibility for the brushing member 3, which is particularly unobstructed due to the low rate of coverage of its active portion that is covered only to the extent that is necessary and sufficient.

In addition, the first and second antinodes 33, 34 advantageously form safeguards that avoid any over-compression of the brushing member 3 against the tooth or against the gum, thereby considerably limiting the risk of injuring said gum or of exerting over-abrasive action at the surface of said tooth.

Finally, the clearance zones 35, 36 allow the head of the brush, and more particularly the brushing member 3, to be re-oriented without the physiological retractor 10 coming into abutment against the tooth or the gum, thereby guaranteeing that the brushing member 3 has access to the recessed nooks such as the interstices between teeth.

The physiological retractor 10 of the invention therefore has a particularly advantageous combination of geometrical characteristics that makes brushing more comfortable, effective, and safe for the user.

SUSCEPTIBILITY OF INDUSTRIAL APPLICATION

The invention is industrially applicable to designing and manufacturing dental hygiene instruments, of the toothbrush type.

The invention claimed is:

1. A toothbrush (1) comprising:
   a.) a support member (2) of the handle type;
   b.) at least one brushing member (3) for brushing teeth, which member is mounted to rotate on said support member (2) about an axis of rotation (X-X'), said brushing member (3) having a side surface (3L) that extends along its axis of rotation (X-X') between a proximal end (3P) facing towards the support member (2), and an opposite, distal end (3D), said side surface (3L) being designed to be brought into contact with the teeth for the purpose of cleaning them by mechanical action; and
   c.) a physiological retractor (10) covering said side surface (3L) in part so as to protect the mucous membranes adjacent to the teeth from the mechanical action of the brushing member (3);
   said toothbrush (1) being characterized in that, facing the side surface (3L) of the brushing member, the physiological retractor (10) has a retraction portion (15), and the distance ($R_E$) from the outside surface (15E) of said retraction portion to said axis (X-X') varies along the axis of rotation (X-X') in such a manner as to form a bulge (20), and in that said physiological retractor (10) has a beveled distal portion (40) forming a penetration tip,
   the angular coverage ($\delta$) of the physiological retractor (10) about the axis of rotation (X-X'), facing the side surface (3L) of the brushing member (3), varies along said axis (X-X'),
   the physiological retractor (10) has first and second cheeks (31, 32) disposed on either side of the brushing member (3) about the axis of rotation (X-X') so that the angular coverage ($\delta$) of the corresponding cross-section is greater than 180°, and preferably strictly greater than 180° and less than or equal to 190°, along the axis (X-X'), the first and second cheeks (31, 32) have respective ones of first and second antinodes (33, 34) that constitute the low points of the physiological retractor (10), and with the brushing member (3) having a length L as measured between its proximal end (3P) and its distal end (3D), the low points (33, 34) are situated in register with a point V on the axis of rotation (X-X') that is situated at a distance (D2) lying in the range 0.3×L to 0.5×L, and preferably substantially equal to 0.4×L, from the distal end (3D).

2. A toothbrush according to claim 1, characterized in that the bulge (20) forms a hoop that is inclined relative to the axis (X-X').

3. A toothbrush according to claim 2, characterized in that, with the brushing member (3) having a length L as measured between its proximal end (3P) and its distal end (3D), the bulge (20) culminates in register with a point S on the axis of rotation (X-X') that is situated at a distance (D1) lying in the range 0.5×L to 0.9×L, and preferably in the range 0.65×L to 0.80×L, from the distal end (3D).

4. A toothbrush according to claim 1, characterized in that, with the brushing member (3) having a length L as measured between its proximal end (3P) and its distal end (3D), the bulge (20) culminates in register with a point S on the axis of rotation (X-X') that is situated at a distance (D1) lying in the range 0.5×L to 0.9×L, and preferably in the range 0.65×L to 0.80×L, from the distal end (3D).

5. A toothbrush according to claim 1, characterized in that the retraction portion (15) has at least a first segment (21) that has a substantially frustoconical outside surface.

6. A toothbrush according to claim 5, characterized in that the retraction portion (15) has at least one second segment (22) that has a substantially frustoconical outside surface.

7. A toothbrush according to claim 6, characterized in that the first and the second segments (21, 22) extend in opposite directions from their common base, so that the outside surface (15E) of the retraction portion (15) is substantially bi-conical in shape.

8. A toothbrush according to claim 1, characterized in that a hoop formed by the bulge (20) joins the first antinode (33) to the second antinode (34) by going via the dorsal maximum of the bulge (20).

9. A toothbrush according to claim 1, characterized in that the penetration tip (40) has two engagement ramps (41, 42), each of which connects the antinode of a respective one of the cheeks (31, 32) to the free distal edge (43) of the physiological retractor (10).

10. A toothbrush according to claim 1, characterized in that the physiological retractor (10) does not extend beyond the distal end (3D) of the brushing member (3) along the axis (X-X').

11. A toothbrush according to claim 1, characterized in that the physiological retractor (10) is open at its distal end so as to expose most of, and preferably all of, the distal end (3D) of the brushing member (3).

12. A toothbrush (1) comprising:
 a.) a support member (2) of the handle type;
 b.) at least one brushing member (3) for brushing teeth, which member is mounted to rotate on said support member (2) about an axis of rotation (X-X'), said brushing member (3) having a side surface (3L) that extends along its axis of rotation (X-X') between a proximal end (3P) facing towards the support member (2), and an opposite, distal end (3D), said side surface (3L) being designed to be brought into contact with the teeth for the purpose of cleaning them by mechanical action; and
 c.) a physiological retractor (10) covering said side surface (3L) in part so as to protect the mucous membranes adjacent to the teeth from the mechanical action of the brushing member (3);

said toothbrush (1) being characterized in that, facing the side surface (3L) of the brushing member, the physiological retractor (10) has a retraction portion (15), and the distance ($R_E$) from the outside surface (15E) of said retraction portion to said axis (X-X') varies along the axis of rotation (X-X') in such a manner as to form a bulge (20), and in that said physiological retractor (10) has a beveled distal portion (40) forming a penetration tip, the angular coverage (δ) of the physiological retractor (10) about the axis of rotation (X-X'), facing the side surface (3L) of the brushing member (3), varies along said axis (X-X'), the physiological retractor (10) has first and second cheeks (31, 32) disposed on either side of the brushing member (3) about the axis of rotation (X-X') so that the angular coverage (δ) of the corresponding cross-section is greater than 180°, and preferably strictly greater than 180° and less than or equal to 190°, along the axis (X-X'), the first and second cheeks (31, 32) have respective ones of first and second antinodes (33, 34) that constitute the low points of the physiological retractor (10), and the physiological retractor (10) has first and second clearance zones (35, 36) disposed on either side of each antinode (33, 34) so as to allow the physiological retractor (10) and the brushing member (3) a certain amount of clearance so that they can rock to some extent about an axis that is transverse to said axis of rotation (X-X').

13. A toothbrush according to claim 12, characterized in that the physiological retractor (10) does not extend beyond the distal end (3D) of the brushing member (3) along the axis (X-X').

14. A toothbrush according to claim 12, characterized in that the physiological retractor (10) is open at its distal end so as to expose most of, and preferably all of, the distal end (3C) of the brushing member (3).

15. A toothbrush (1) comprising:
 a.) a support member (2) of the handle type;
 b.) at least one brushing member (3) for brushing teeth, which member is mounted to rotate on said support member (2) about an axis of rotation (X-X'), said brushing member (3) having a side surface (3L) that extends along its axis of rotation (X-X') a proximal end (3P) facing towards the support member (2), and an opposite, distal end (3D), said side surface (3L) being designed to be brought into contact with the teeth for the purpose of cleaning them by mechanical action; and
 c.) a physiological retractor (10) covering said side surface (3L) in part so as to protect the mucous membranes adjacent to the teeth from the mechanical action of the brushing member (3);

said toothbrush (1) being characterized in that, facing the side surface (3L) of the brushing member, the physiological retractor (10) has a retraction portion (15), and the distance ($R_E$) from the outside surface (15E) of said retraction portion to said axis (X-X') varies along the axis of rotation (X-X') in such a manner as to form a bulge (20), and in that said physiological retractor (10) has a beveled distal portion (40) forming a penetration tip, the angular coverage (δ) of the physiological retractor (10) about the axis of rotation (X-X'), facing the side surface (3L) of the brushing member (3), varies along said axis (X-X'), the physiological retractor (10) has first and second cheeks (31, 32) disposed on either side of the brushing member (3) about the axis of rotation (X-X') so that the angular coverage (δ) of the corresponding cross-section is greater than 180°, and preferably strictly greater than 180° and less than or equal to 190°, along the axis (X-X'), the first and second cheeks (31, 32) have respective ones of first and second antinodes (33, 34) that constitute the low points of the physiological retractor (10), the physiological retractor (10) has first and second clearance zones (35, 36) disposed on either side of each antinode (33, 34) so as to allow the physiological retractor (10) and the brushing member (3) a certain amount of clearance so that they can rock to some extent about an axis that is transverse to said axis of rotation (X-X'), and a hoop formed by the bulge (20) joins the first antinode (33) to the second antinode (34) by going via the dorsal maximum of the bulge (20).

\* \* \* \* \*

UNITED STATES PATENT AND TRADEMARK OFFICE
CERTIFICATE OF CORRECTION

PATENT NO.       : 8,590,093 B2                         Page 1 of 1
APPLICATION NO.  : 12/988498
DATED            : November 26, 2013
INVENTOR(S)      : Thierry André Christian Vallet It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this
Twenty-second Day of September, 2015

Michelle K. Lee
*Director of the United States Patent and Trademark Office*